(12) United States Patent
Binah et al.

(10) Patent No.: US 8,263,655 B2
(45) Date of Patent: Sep. 11, 2012

(54) METHODS FOR TREATMENT OF RENAL FAILURE

(75) Inventors: Ofer Binah, Nofit (IL); Zaid A. Abassi, Haifa (IL); Moussa B. H. Youdim, Haifa (IL); Yaron Barac, Kiryat Motzkin (IL)

(73) Assignees: Technion Research and Development Foundation Ltd, Haifa (IL); Rappaport Family Institute, Haifa (IL)

( * ) Notice: Subject to any disclaimer, the term of this patent is extended or adjusted under 35 U.S.C. 154(b) by 606 days.

(21) Appl. No.: 11/244,150

(22) Filed: Oct. 6, 2005

(65) Prior Publication Data

US 2007/0082958 A1    Apr. 12, 2007

(51) Int. Cl.
*A61K 31/135* (2006.01)
*A61K 31/185* (2006.01)

(52) U.S. Cl. .................. 514/558; 514/183; 514/649

(58) Field of Classification Search .................. None
See application file for complete search history.

(56) References Cited

U.S. PATENT DOCUMENTS

| | | | |
|---|---|---|---|
| 3,297,527 A | 1/1967 | Elslager |
| 4,861,800 A | 8/1989 | Buyske |
| 5,151,419 A | 9/1992 | Perenyi et al. |
| 5,151,449 A | 9/1992 | Milgram |
| 5,169,868 A | 12/1992 | Yu et al. |
| 5,192,808 A | 3/1993 | Ruehl et al. |
| 5,225,446 A | 7/1993 | Milgram |
| 5,242,950 A | 9/1993 | Fries Hastings |
| 5,276,057 A | 1/1994 | Milgram et al. |
| 5,387,612 A | 2/1995 | Youdim et al. |
| 5,387,615 A | 2/1995 | Milgram et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,639,913 A | 6/1997 | Lidor et al. |
| 5,668,181 A | 9/1997 | Youdim et al. |
| 5,744,500 A | 4/1998 | Youdim et al. |
| 5,786,390 A | 7/1998 | Youdim et al. |
| 5,840,979 A | 11/1998 | Durden et al. |
| 5,891,923 A | 4/1999 | Youdim et al. |
| 6,251,938 B1 | 6/2001 | Chorev et al. |
| 6,251,950 B1 | 6/2001 | Durden et al. |
| 6,277,886 B1 | 8/2001 | Levy et al. |
| 6,303,650 B1 | 10/2001 | Chorev et al. |
| 6,316,504 B1 | 11/2001 | Youdim et al. |
| 6,395,780 B1 | 5/2002 | Arlt et al. |
| 6,462,222 B1 | 10/2002 | Chorev et al. |
| 6,538,025 B2 | 3/2003 | Chorev et al. |
| 6,562,365 B2 | 5/2003 | Blume et al. |
| 2002/0019421 A1 | 2/2002 | Biberman |
| 2002/0137786 A1 | 9/2002 | Tatton et al. |
| 2002/0188020 A1 | 12/2002 | Chorev et al. |
| 2005/0171210 A1* | 8/2005 | Youdim et al. ............ 514/657 |

FOREIGN PATENT DOCUMENTS

WO    WO 92/17169 A1    10/1992
WO    WO 92/21333 A2    12/1992

OTHER PUBLICATIONS

Eliash et al., "Rasagiline and its (S) enantiomer increase survival and prevent stroke in salt-loaded stroke-prone spontaneously hypertensive rats," 2001, J Neural Transm, vol. 108, pp. 909-923.*
Sillilx et al., Crit. Care Clin., 1987, 3, 1 page.*
Thadhani et al., New. Eng. J. Medicine, 1996, 334(22), 1448-1460.*
Agraharkar et al., http://emedicine.medscape.com/article/243492-overview, 1-9.*
Merck, Chronic kidney disease, defintion, 1-8.*
Merck, Acute kidney disease definition, 1-9.*
Woodrow et al., Postgrad Med J, 1994, 192-194.*
Grone, Nephrol Dial Transplant, 1999, 14, 1595-1598.*
Abuelo et al., "Normotensive Ischemic Acute Renal Failure", N Engl J Med 357;8, pp. 797-805 (2007).
Ashkenazi et al., "Prehospital Management of Earthquake Casualties Buried Under Rubble", Prehosp Disaster Med., 20, 122-133 (2005).
Bellomo et al., "Defining and classifying acute renal failure: from advocacy to consensus and validation of the RIFLE criteria", Intensive Care Med 33:409-413 (2007).
Better et al., "Early management of Shock and Prophylaxis of Acute Renal Failure in Traumatic Rhabdomyolysis" N Engl J. Med, 322, 825-829 (1990).
Better et al., "Muscle crush compartment syndrome: Fulminant local edema with threatening systemic effects", Kidney International, vol. 63, pp. 1155-1157 (2003).
Better et al., "History of the Crush Syndrome: From the Earthquakes of Messina, Sicily 1909 to Spitak, Armenia 1988", Am J. Nephrol, 17:392-394 (1997).
Brady et al.,"Acute renal failure" Lancet, 346, 1533-1540 (1995).
Chatterjee., "Novel pharmacological approaches to the treatment of renal ischemia-reperfusion injury: a comprehensive review" Naunyn-Schmiedeberg's Arch Pharmacol 376:1-43 (2007).
Devarajan.,"Update on Mechanisms of Ischemic Acute Kidney Injury" J Am Soc Nephrol 17: 1503-1520 (2006).
El Kossi et al., "Epidemiology and Pathophysiology of Chronic Kidney Disease: Natural History, Risk Factors, and Management" Comprehensive Clinical Nephrology Textbook, Edited by Richard J. Johnson MD and John Feehally MD, Mosby Publisher, Chapter 68, pp. 813-821 (2007).
Haddad et al., "Retarding Progression of Kidney Disease" Comprehensive Clinical Nephrology Textbook, Edited by Richard J. Johnson MD and John Feehally MD, Mosby Publisher, Chapter 69, pp. 823-829 (2007).
Hirsch "Preventing end-stage renal disease: flexible strategies to overcome obstacles", Curr Opin Nephrol Hypertens 15:473-480 (2006).
Lameire et al., "Epidemiology, Clinical Evaluation, and Prevention of Acute Renal Failure" Comprehensive Clinical Nephrology Textbook, Edited by Richard J. Johnson MD and John Feehally MD, Mosby Publisher, Chapter 64, pp. 771-784 (2007).

(Continued)

Primary Examiner — David J Blanchard
Assistant Examiner — Kyle Purdy
(74) Attorney, Agent, or Firm — Browdy and Neimark, PLLC (57) ABSTRACT

Propargylamine, propargylamine derivatives N-propargyl-1-aminoindan and analogs thereof, and pharmaceutically acceptable salts thereof, are useful for administration to a subject at high risk for or suffering from acute renal failure (ARF).

12 Claims, 6 Drawing Sheets

OTHER PUBLICATIONS

Lehmann., "Angiotensin-Converting Enzyme Inhibitors May Cause Renal Dysfunction in Patients on Long-Term Lithium Treatment" American Journal of Kidney Diseases, vol. 25, No. 1, pp. 82-87 (1995).

Reis et al., "Mechanical muscle-crush injury and acute muscle-crush compartment syndrome with special reference to earthquake casualties" J Bone Joint Surg [Br] 87-B:450-3 (2005).

Rubinstein et al., "Involvement of Nitric Oxide System in Experimental Muscle Crush Injury" J. Clin Invest, vol. 101, No. 6, pp. 1325-1333 (1998).

Rubinstein et al., "Hyperbaric oxygen treatment improves GFR in rats with ischaemia/reperfusion renal injury: a possible role for the antioxidant/oxidant balance in the ischaemic kidney" J Nephrol Dial Transplant, 24: 428-436 (2009).

Schrier et al., "Acute Renal Failure and Sepsis" N. Engl. J. Med, 351, pp. 159-169 (2004).

Schrier et al., "Acute renal failure: definitions, diagnosis, pathogenesis, and therapy" J. Clin. Invest, 114, pp. 5-14 (2004).

Shigehiko et al., "Acute Renal Failure in Critically Ill Patients, A Multinational, Multicenter Study" JAMA, 294, pp. 813-818 (2005).

Swan et al., "Clinical Pharmacology for the Nephrologist" NephSAP, 9, 220-271 (2010).

Warnock., "Towards a Definition and Classification of Acute Kidney Injury", J Am Soc Nephrol 16: 3149-3150 (2005).

Wheeler., "Clinical Evaluation and Management of Chronic Kidney Disease" Comprehensive Clinical Nephrology Textbook, Edited by Richard J. Johnson MD and John Feehally MD, Mosby Publisher, Chapter 70, pp. 831-837 (2007).

\* cited by examiner

METHODS FOR TREATMENT OF RENAL FAILURE

FIELD OF THE INVENTION

The present invention relates to methods and compositions for the treatment of renal failure and, more particularly, to propargylamine and derivatives thereof for use in said compositions and methods.

BACKGROUND OF THE INVENTION

Congestive Heart Failure

Congestive heart failure (CHF) is characterized by activation of neurohormonal systems such as the renin-angiotensin, sympathetic nervous system and vasopressin. It is commonly accepted that increased activity of these three vasoconstrictor systems plays a major role in the pathophysiology of CHF and may contribute to the clinical deterioration of patients with this syndrome. In particular, it has been documented that neurohormonal activation may have detrimental effects on the cardiovascular system and on the kidney. These include systemic vasoconstriction with increased afterload and the development of cardiac hypertrophy. In addition, neurohormonal activation may lead to deterioration in renal function, renal vasoconstriction, salt and water retention, and consequently edema formation (Dzau, 1987).

Cardiac hypertrophy is a major risk factor of cardiovascular mortality and morbidity (de Simone et al, 2001). It is a general adaptive response to states of hyperfunction (Meerson et al, 1996), and is observed in a wide variety of physiological and pathologic states, including pressure overload, volume overload, and excessive exposure to neurohumoral and metabolic stimuli. At its first stages, hypertrophy is a compensatory response. With the progression of the initial stimulus, a transition occurs in which an irreversible decompensation in cardiac function takes place, leading to heart failure, as well as to an increased tendency to develop arrhythmias (Chien, 1999; Swynghedauw and Baillard, 2000). The trigger for this transition from compensated hypertrophy to decompensation is unknown. Morphological and histological analyses reveal that decompensated hypertrophy and heart failure are usually characterized by ventricular dilation and collagen deposition, resulting in cardiac fibrosis and, subsequently, in myocardial stiffness.

Although of great importance, the mechanisms underlying the cardiac hypertrophy and fibrotic response remain poorly understood. It has been suggested that both the circulating and local myocardial neurohumoral systems such as renin-angiotensin-aldosterone system (RAAS) play a role in the development of ventricular hypertrophy and fibrosis (Dzau, 1987; Watkins et al, 1976). Similarly, activation of the sympathetic nervous system contributes to sodium retention, and to cardiac hypertrophy and fibrosis in clinical and experimental heart failure (Hostetter et al., 1983; Abassi et al. 1990; Brodsky et al., 1998).

Renal Failure

Acute renal failure (ARF) is a syndrome characterized by a sudden decrease in kidney function leading to a decrease or sudden loss of the ability of the kidneys to excrete wastes, concentrate urine, conserve electrolytes and maintain fluid balance. It is a frequent clinical problem, particularly in the intensive care unit, where it is associated with a mortality of between 50% and 80% (Schrier et al, 2004). ARF may occur following exposure to various therapeutic agents such as cyclosporine, aminoglycosides, nonsteroidal antiinflammatory drugs, cisplatin, amphotericin B, or procedures, e.g., radiocontrast media, or exposure to heavy metal, which inflict toxic and ischemic damage to the renal tissue (Green et al, 2000).

The mechanisms underlying ARF involve both vascular and tubular factors (Kribben et al, 1999). An ischemic insult to the kidney due to hypoperfusion will, in general, be the cause of the ARF. While a decrease in renal blood flow with diminished oxygen and substrate delivery to the tubule cells is an important ischemic factor, it must be remembered that a relative increase in oxygen demand by the tubule is also a factor in renal ischemia. Renal ischemia leads to a series of cellular events which might culminate in organ failure, depending on the cell type and the duration of ischemia. It was assumed that reperfusion, instituted before irreversible damage to the tissue occurred, would limit the insult to the organ. Contrary to such expectations, it was reported that reperfusion enhances renal damage (Canavese et al., 1988). Several suggestions for the basis of this 'reperfusion injury' have been proposed. It has been linked to an attenuated restoration in renal blood flow which returns only to 60% of its preischemic value (Arendshorst et al., 1975; Cristol et al., 1993). Others have suggested that reactive oxygen species (ROS) generated during ischemia and reperfusion in the mitochondria, cause the damage (Canavese et al., 1988; Greene et al., 1991).

Chronic renal failure (CRF) is the progressive loss of kidney function. The kidneys attempt to compensate for renal damage by hyperfiltration (excessive straining of the blood) within the remaining functional nephrons (filtering units that consist of a glomerulus and corresponding tubule). Over time, hyperfiltration causes further loss of function.

Chronic loss of function causes generalized wasting (shrinking in size) and progressive scarring within all parts of the kidneys. In time, overall scarring obscures the site of the initial damage. Yet, it is not until over 70% of the normal combined function of both kidneys is lost that most patients begin to experience symptoms of kidney failure.

Propargylamine and Propargylamine Derivatives

Rasagiline, R(+)-N-propargyl-1-aminoindan, a highly potent selective irreversible monoamine oxidase (MAO)-B inhibitor, has been shown to exhibit neuroprotective activity and antiapoptotic effects against a variety of insults in cell cultures and in vivo.

Rasagiline is being developed for Parkinson's disease as monotherapy or as an adjunct to L-dopa therapy (Youdim et al., 2001; Parkinson Study Group, 2002; Finberg and Youdim, 2002; Gassen et al., 2003). Phase III controlled studies have shown that rasagiline is effective with a dose of as low as 1 mg/kg in monotherapy (Parkinson Study group, 2002) and as an adjunct to L-dopa, comparable in its effect to the anti-Parkinson catechol-O-methyltranferase (COMT) inhibitor, entacapone (Brooks and Sagar, 2003). Rasagiline has recently finished the phase III clinical trials and has been approved for Parkinson's disease.

Rasagiline exhibits neuroprotective activities both in vitro and in vivo (for review see Mandel et al., 2003; Youdim et al., 2003) which may contribute to its possible disease modifying activity. It is metabolized to its major two metabolites: aminoindan (TVP-136) and S(−)-N-propargyl-1-aminoindan (TVP-1022) (Youdim et al., 2001), which also have neuroprotective activity against serum deprivation and 1-methamphetamine-induced neurotoxicity in partially differentiated PC-12 cells (Am et al., 2004).

By contrast, selegiline (1-deprenyl), a selective MAO-B inhibitor which is a useful anti-Parkinson drug both in monotherapy (Parkinson Study Group, 1989) and as an adjunct to L-DOPA therapy, and has L-DOPA sparing action (Birkmayer et al., 1977; Riederer and Rihne, 1992; Parkinson Study Group, 1989), is a propargyl derivative of 1-methamphetamine. Thus, the major metabolite of selegiline, 1-methamphetamine (Szoko et al., 1999; Kraemer and Maurer, 2002; Shin, 1997), is neurotoxic (Abu-Raya et al., 2003; Am et al., 2004). In contrast to aminoindan, L-methamphetamine prevents the neuroprotective activities of rasagiline and selegiline in partially differentiated cultured PC-12 cells (Am et al., 2004).

Selegiline and methamphetamine, unlike rasagiline and aminoindan, have sympathomimetic activity (Simpson, 1978) that increases heart rate and blood pressure (Finberg et al., 1990; Finberg et al., 1999). Recent studies (Glezer and Finberg, 2003) have indicated that the sympathomimetic action of selegiline can be attributed to its 1-methamphetamine and amphetamine metabolites. These properties are absent in rasagiline and in its metabolite aminoindan. Parkinsonian patients receiving combined treatments with selegiline plus levodopa have been reported to have a higher mortality rate than those treated with levodopa alone (Lees, 1995). This is not related to its MAO-B inhibitory activity, but rather attributed to its sympathomimetic action and methamphetamine metabolites (Reynolds et al., 1978; Lavian et al., 1993).

Several propargylamine derivatives have been shown to selectively inhibit MAO-B and/or MAO-A activity and, thus to be suitable for treatment of neurodegenerative diseases such as Parkinson's and Alzheimer's disease. In addition, these compounds have been further shown to protect against neurodegeneration by preventing apoptosis.

R(+)-N-propargyl-1-aminoindan and pharmaceutically acceptable salts thereof were first disclosed in U.S. Pat. Nos. 5,387,612, 5,453,446, 5,457,133, 5,576,353, 5,668,181, 5,786,390, 5,891,923, and 6,630,514 as useful for the treatment of Parkinson's disease, memory disorders, dementia of the Alzheimer type, depression, and the hyperactive syndrome. The 4-fluoro-, 5-fluoro- and 6-fluoro-N-propargyl-1-aminoindan derivatives were disclosed in U.S. Pat. No. 5,486,541 for the same purposes.

U.S. Pat. Nos. 5,519,061, 5,532,415, 5,599,991, 5,744,500, 6,277,886, 6,316,504, 133, U.S. Pat. Nos. 5,576,353, 5,668,181, 5,786,390, 5,891,923, and 6,630,514 disclose R(+)-N-propargyl-1-aminoindan and pharmaceutically acceptable salts thereof as useful for treatment of additional indications, namely, an affective illness, a neurological hypoxia or anoxia, neurodegenerative diseases, a neurotoxic injury, stroke, brain ischemia, a head trauma injury, a spinal trauma injury, schizophrenia, an attention deficit disorder, multiple sclerosis, and withdrawal symptoms.

U.S. Pat. No. 6,251,938 describes N-propargyl-phenylethylamine compounds, and U.S. Pat. Nos. 6,303,650, 6,462,222 and 6,538,025 describe N-propargyl-1-aminoindan and N-propargyl-1-aminotetralin compounds, said to be useful for treatment of depression, attention deficit disorder, attention deficit and hyperactivity disorder, Tourette's syndrome, Alzheimer's disease and other dementia such as senile dementia, dementia of the Parkinson's type, vascular dementia and Lewy body dementia.

The first compound found to selectively inhibit MAO-B was R-(−)-N-methyl-N-(prop-2-ynyl)-2-aminophenylpropane, also known as L-(−)-deprenyl, R-(−)-deprenyl, or selegiline. In addition to Parkinson's disease, other diseases and conditions for which selegiline is disclosed as being useful include: drug withdrawal (WO 92/21333, including withdrawal from psychostimulants, opiates, narcotics, and barbiturates); depression (U.S. Pat. No. 4,861,800); Alzheimer's disease and Parkinson's disease, particularly through the use of transdermal dosage forms, including ointments, creams and patches; macular degeneration (U.S. Pat. No. 5,242,950); age-dependent degeneracies, including renal function and cognitive function as evidenced by spatial learning ability (U.S. Pat. No. 5,151,449); pituitary-dependent Cushing's disease in humans and nonhumans (U.S. Pat. No. 5,192,808); immune system dysfunction in both humans (U.S. Pat. No. 5,387,615) and animals (U.S. Pat. No. 5,276,057); age-dependent weight loss in mammals (U.S. Pat. No. 5,225,446); schizophrenia (U.S. Pat. No. 5,151,419); and various neoplastic conditions including cancers, such as mammary and pituitary cancers. WO 92/17169 discloses the use of selegiline in the treatment of neuromuscular and neurodegenerative disease and in the treatment of CNS injury due to hypoxia, hypoglycemia, ischemic stroke or trauma. In addition, the biochemical effects of selegiline on neuronal cells have been extensively studied (e.g., see Tatton, et al., 1991 and 1993). U.S. Pat. No. 6,562,365 discloses the use of desmethylselegiline for selegiline-responsive diseases and conditions.

U.S. Pat. Nos. 5,169,868, 5,840,979 and 6,251,950 disclose aliphatic propargylamines as selective MAO-B inhibitors, neuroprotective and cellular rescue agents. The lead compound, (R)-N-(2-heptyl)methyl-propargylamine (R-2HMP), has been shown to be a potent MAO-B inhibitor and anti-apoptotic agent (Durden et al., 2000).

Propargylamine was reported many years ago to be a mechanism-based inhibitor of the copper-containing bovine plasma amine oxidase (BPAO), though the potency was modest. U.S. Pat. No. 6,395,780 discloses propargylamine as a weak glycine-cleavage system inhibitor. Copending U.S. patent application Ser. No. 10/952,379 discloses that propargylamine exhibits neuroprotective and anti-apoptotic activities and can, therefore, be used for all known uses of rasagiline and similar drugs containing the propargylamine moiety.

Copending U.S. patent application Ser. No. 10/952,367 of the present applicants discloses and claims a method for treatment of a cardiovascular disorder or disease which comprises administering to the subject an amount of an active agent selected from the group consisting of propargylamine, a propargylamine derivative, and a pharmaceutically acceptable salt thereof.

All and each of the above-mentioned US patents and patent applications are herewith incorporated by reference in their entirety as if fully disclosed herein.

To the best of our knowledge, the renal effects of rasagiline and its metabolites were not disclosed nor examined.

SUMMARY OF THE INVENTION

Since rasagiline is a new anti-Parkinson drug with neuroprotective activity and promising clinical value, our aims were to examine for the first time the acute and chronic effects of rasagiline and its metabolites on: (i) renal clearance and excretory function in rats with renal ischemia, and (ii) on renal functions in rats with experimental heart failure. We have then found that rasagiline and its S-enantiomer S(−)-N-propargyl-1-aminoindan produced significant diuretic and natriuretic responses in association with glomerular filtration rate (GFR) in rats with congestive heart failure, and induced diuretic and natriuretic responses accompanied by improved GFR in the ischemic kidney.

The present invention thus relates to a method for treatment of a subject susceptible to or suffering from renal failure, which comprises administering to the subject an amount of an agent selected from the group consisting of propargylamine, a propargylamine derivative and a pharmaceutically acceptable salt thereof, effective to treat the subject.

The renal failure to be treated may be acute renal failure (ARF) or chronic renal failure (CRF).

In one preferred embodiment of the invention, the agent is a propargylamine derivative, preferably N-propargyl-1-aminoindan or an enantiomer thereof such as R(+)-N-propargyl-1-aminoindan or a pharmaceutically acceptable salt thereof and, more preferably, its enantiomer S-(−)-N-propargyl-1-aminoindan or a pharmaceutically acceptable salt thereof.

DETAILED DESCRIPTION OF THE INVENTION

The present invention relates to a method for treatment of a subject susceptible to or suffering from renal failure which comprises administering to the subject an amount of an active agent selected from the group consisting of propargylamine, a propargylamine derivative, and a pharmaceutically acceptable salt thereof, effective to treat the subject.

In one embodiment, the method of the invention may be used for the treatment of acute renal failure (ARF), independently of its cause and of its type.

In another embodiment, the method of the invention may be used for the treatment of chronic renal failure (CRF), independently of its cause and of its type.

Depending on the localization or the nature of the renal insult, ARF and RCF may be classified as prerenal, renal or postrenal ARF or CRF.

ARF is a syndrome characterized by a sudden decrease of the glomerular filtration rate (GFR) and consequently an increase in blood nitrogen products (blood urea nitrogen and creatinine). Prerenal ARF may be caused, for example, by myocarditis, myocardial infarction, congestive heart failure, arrhythmia, pericardial tamponade, pulmonary embolism, decreased extracellular fluid volume, excessive diuresis, hemorrhage, vomiting, diarrhea, sepsis, peritonitis, pancreatitis, burns, etc. The condition is reversible if the underlying disease is resolved. Parenchymatous or renal ARF are caused, for example, by acute tubular necrosis or injury resulting from cardiovascular surgery, sepsis, exposure to toxic substances and nephrotoxic drugs, accumulation of endogenous nephrotoxins, hemoglobinuria, or intrarenal precipitation (hypercalcemia, urates, sulfonamides, acyclovir, myeloma protein), or by acute glomerulonephritis. Obstructive or postrenal ARF may be caused by congenital abnomalies, acquired uropathies, malignant diseases, some drugs, infections, and others.

CRF is the progressive loss of kidney function. The cause(s) of CRF may be difficult if not impossible to be determined. Prerenal conditions such as poor cardiac function, chronic liver failure, and atherosclerosis ("hardening") of the renal artery may induce ischemic nephropathy. Interference with the normal flow of urine can produce backpressure within the kidneys, can damage nephrons, and lead to obstructive uropathy, a disease of the urinary tract. Abnormalities that may hamper urine flow and cause post-renal CRF include bladder outlet obstruction, kidney stones, and obstruction of the tubules. Renal CFR is caused by changes within the kidneys and include diabetic nephropathy, chronic glomerular nephritis, chronic interstitial nephritis, vasculitis, renal vascular CRF In one preferred embodiment, the active agent used in the present invention is N-propargyl-1-aminoindan, either in its racemic form (described, for example, in U.S. Pat. No. 6,630,514) or as the R-enantiomer R(+)-N-propargyl-1-aminoindan (described, for example, in U.S. Pat. No. 5,387,612) or as the S-enantiomer S-(−)-N-propargyl-1-aminoindan (described, for example, in U.S. Pat. No. 6,277,886). In more preferred embodiments of the invention, the active agent is rasagiline, the R(+)-N-propargyl-1-aminoindan, or its enantiomer S(−)-N-propargyl-1-aminoindan.

In another preferred embodiment, the active agent is a pharmaceutically acceptable salt of N-propargyl-1-aminoindan or of an enantiomer thereof including, but not limited to, the mesylate, maleate, fumarate, tartrate, hydrochloride, hydrobromide, esylate, p-toluenesulfonate, benzoate, acetate, phosphate and sulfate salts. In preferred embodiments, the salt is a pharmaceutically acceptable salt of R(+)-N-propargyl-1-aminoindan such as, but not limited to, the mesylate salt (described, for example, in U.S. Pat. No. 5,532,415), the esylate and the sulfate salts (both described, for example, in U.S. Pat. No. 5,599,991), and the hydrochloride salt (described, for example, in U.S. Pat. No. 6,630,514) of R(+)-N-propargyl-1-aminoindan or S(−)-N-propargyl-1-aminoindan.

In a further embodiment, the active agent is an analog of N-propargyl-1-aminoindan, an enantiomer or a pharmaceutically acceptable salt thereof. In one embodiment, the analogs are the compounds described in U.S. Pat. No. 5,486,541 such as, but not limited to, the compounds 4-fluoro-N-propargyl-1-aminoindan, 5-fluoro-N-propargyl-1-aminoindan, 6-fluoro-N-propargyl-1-aminoindan, an enantiomer thereof and pharmaceutically acceptable addition salts thereof. In another embodiment, the analogs are the compounds described in U.S. Pat. No. 6,251,938 such as, but not limited to, the compounds (rac)-3-(N-methyl,N-propyl-carbamyloxy)-α-methyl-N'-propargyl phenethylamine HCl; (rac)-3-(N,N-dimethyl-carbamyloxy)-α-methyl-N'-methyl, N'-propargyl phenethylamine HCl; (rac)-3-(N-methyl,N-hexyl-carbamyloxy)-α-methyl-N'-methyl, N'-propargyl phenethylamine mesylate; (rac)-3-(N-methyl,N-cyclohexyl-carbamyloxy)-α-methyl-N'-methyl,N'-propargylphenethyl HCl; and (S)-3-(N-methyl,N-hexyl-carbamyloxy)-α-methyl-N'-methyl,N'-propargyl phenethylamine ethane-sulfonate. In a further embodiment, the analogs are the compounds described in U.S. Pat. No. 6,303,650 such as, but not limited to, the compounds (rac) 6-(N-methyl, N-ethyl-carbamyloxy)-N'-propargyl-1-aminoindan HCl; (rac) 6-(N,N-dimethyl, carbamyloxy)-N'-methyl-N'-propargyl-1-aminoindan HCl; (rac) 6-(N-methyl, N-ethyl-carbamyloxy-N'-propargyl-1-aminotetralin HCl; (rac) 6-(N,N-dimethyl-thiocarbamyloxy)-1-aminoindan HCl; (rac) 6-(N-propyl-carbamyloxy-N'-propargyl-1-aminoindan HCl; (rac) 5-chloro-6-(N-methyl,N-propyl-carbamyloxy)-N'-propargyl-1-aminoindan HCl; (S)-6-(N-methyl), N-propyl-carbamyloxy)-N'-propargyl-1-aminoindan HCl; and (R)-6-(N-methyl,N-ethyl-carbamyloxy)-N'-propargyl-1-aminoindan hemi-(L)-tartrate, and 6-(N-methyl,N-ethyl-carbamyloxy)-N'-methyl,N'-propargyl-1-aminoindan described in U.S. Pat. No. 6,462,222.

In a still further embodiment, the active agent is an aliphatic propargylamine described in U.S. Pat. Nos. 5,169,868, 5,840,979 and 6,251,950 such as, but not limited to, the compounds N-(1-heptyl)propargylamine; N-(1-octyl)propargylamine; N-(1-nonyl)propargylamine; N-(1-decyl)propargylamine; N-(1-undecyl)propargylamine: N-(1-dodecyl)propargylamine; R—N-(2-butyl)propargylamine; R—N-(2-pentyl)propargylamine; R—N-(2-hexyl)propargylamine; R—N-(2-heptyl)propargylamine; R—N-(2-octyl)propargylamine; R—N-(2-nonyl)propargylamine; R—N-(2-decyl)propargylamine, R—N-(2-undecyl)propargylamine; R—N-(2-dodecyl)propargylamine: N-(1-butyl)-N-methylpropargylamine; N-(2-butyl)-N-methylpropargylamine; N-(2-pentyl)-N-methylpropargylamine; N-(1-pentyl)-N-methylpropargylamine; N-(2-hexyl)-N-methylpropargylamine; N-(2-heptyl)-N-methylpropargylamine; N-(2-decyl)-N-methylpropargylamine; N-(2-dodecyl)-N-methylpropargylamine; R(−)-N-(2-butyl)-N-methylpropargylamine; or a pharmaceutically acceptable salt thereof.

In yet another embodiment, the active agent is selegiline, desmethylselegiline or norprenyl, pargyline or chlorgyline.

In still another embodiment, the active agent is the compound (N-methyl-N-propargyl-10-aminomethyl-dibenzo[b,f]oxepin (known as CGP 3466, described in Zimmermann et al., 1999).

All the US patents and other publications mentioned hereinabove are hereby incorporated by reference in their entirety as if fully disclosed herein.

For use in the method of the present invention, a pharmaceutical composition is provided for prevention and/or treatment of renal failure comprising a pharmaceutically acceptable carrier and an agent selected from the group consisting of propargylamine, a propargylamine derivative, or a pharmaceutically acceptable salt thereof as described above.

The pharmaceutical composition provided by the present invention may be in solid, semisolid or liquid form and may further include pharmaceutically acceptable fillers, carriers or diluents, and other inert ingredients and excipients. The composition can be administered by any suitable route, e.g. intravenously, orally, parenterally, rectally, or transdermally. The dosage will depend on the state of the patient and severity of the disease and will be determined as deemed appropriate by the practitioner.

In one embodiment, the pharmaceutically acceptable carrier is a solid and the pharmaceutical composition is in a suitable form for oral administration including tablets, compressed or coated pills, dragees, sachets, hard or soft gelatin capsules, and sublingual tablets. In a more preferred embodiment, the pharmaceutical composition is a tablet containing an amount of the active agent in the range of about 0.1-100 mg, preferably from about 1 mg to about 10 mg.

In another embodiment, the pharmaceutically acceptable carrier is a liquid and the pharmaceutical composition is an injectable solution. The amount of the active agent in the injectable solution is in the range of from about 0.1 mg to about 100 mg per injection, more preferably 1 mg to about 10 mg per injection.

For parenteral administration the invention provides ampoules or vials that include an aqueous or non-aqueous solution or emulsion. For rectal administration there are provided suppositories with hydrophilic or hydrophobic (gel) vehicles.

The dosage and frequency of administration of the drug will depend from the age and condition of the patient, type of disorder and its severity, and will be determined according to the physician's judgment.

In one embodiment of the invention, the active agent is administered alone. In other embodiments of the invention, the active agent is administered in combination with another known drug for treatment of renal failure, either before, simultaneously or after said other drug.

The following examples illustrate certain features of the present invention but are not intended to limit the scope of the present invention.

The invention will now be illustrated by the following non-limiting Examples.

EXAMPLES

Material and Methods (i) Materials. Rasagiline and its enantiomer S(−)-N-propargyl-1-aminoindan were kindly donated by Teva Pharmaceutical Industries Ltd. (Petach Tikva, Israel).

(ii) Animals. Studies were conducted on Sprague Dawley rats (Harlan Laboratories Ltd., Jerusalem, Israel), weighing 290~330 g. The animals were kept in a temperature-controlled room, and were fed standard rat chow containing 0.5% NaCl and tap water ad libitum. All experiments were performed according to the guidelines of the Technion Committee for Supervision of Animal Experiments (Haifa, Israel). Rats were subjected to one of the experimental protocols, described in Examples 1 and 2 hereinafter.

(iii) Chemical analysis. Sodium concentration in plasma and urine was determined by flame photometry (model IL 943, Instrumentation Laboratory). Inulin and creatinine concentrations were determined by the colorimetric anthrone method. Glomerular filtration rate (GFR) was equated with the clearance of inulin or creatinine.

(iv) Statistical analysis. Statistical significance was assessed by one-way analysis of variance (ANOVA), ANOVA for repeated measures, or two-way ANOVA, as appropriate. The Dunnett test and Tukey's multiple comparisons test were used for data point comparisons of each group. $P<0.05$ was considered statistically significant. Data are presented as means±S.E.M.

In the following experiments, our aim was to examine the efficacy of rasagiline and its S-isomer, S(−)-N-propargyl-1-aminoindan, in two different experimental protocols: (i) Renoprotective efficacy in renal ischemia; and (ii) Renal function in rats with experimental heart failure.

Example 1

Acute Studies—Effects of Rasagiline or S-(−)-N-propargyl-1-aminoindan on Renal Clearance Parameters in Rats with Renal Ischemia This protocol was designed to assess the reno-protective effects of rasagiline and S-(−)-N-propargyl-1-aminoindan in a rat renal ischemia-reperfusion injury (IRI) model of acute renal failure (ARF). For this purpose, the effects of either rasagiline or S-(−)-N-propargyl-1-aminoindan on renal clearance parameters, i.e., glomerular filtration rate (GFR), absolute and fractional sodium excretion rates ($U_{Na}V$ and $FE_{Na}$, respectively), and urinary flow (V) were studied in rats that underwent renal ischemia. Rats that underwent the same procedure, but were treated with vehicle, served as controls.

The surgical procedure for the induction of renal ischemia has been previously described (Sela et al., 1992). Briefly, the animals were anesthetized with Inactin (100 mg/kg, i.p.), placed on a thermo-regulated (37° C.) surgical table and prepared for hemodynamic and clearance studies (Brodsky et al., 1998). After tracheotomy, polyethylene tubes ($PE_{50}$) were inserted into the carotid artery, jugular vein and urinary bladder for blood pressure monitoring, infusion of various solutions and urine collections, respectively. A solution of 2% inulin in 0.9% saline was infused throughout the experiment at a rate of 1.0% of body weight per hour. After surgery and a 60-minute equilibration period, two baseline clearance periods of 30 minutes each were obtained. Then, the left kidney was exposed and the renal artery was clamped for forty-five minutes of ischemia, followed by 60 min of reperfusion. The right kidney served as the control, for each animal. Thirty minutes prior to the induction of the renal ischemia, animals were treated with either rasagiline or S-(−)-N-propargyl-1-aminoindan administered as a bolus injection (1.0 mg/kg, I.V.), followed by a sustained infusion of the drugs at a dose of 2 mg/kg/h throughout the whole experiment. Animals treated with saline served as controls. Then, two additional clearance periods were obtained under the influence of the drug. Urine volume was determined gravimetrically. Blood samples were obtained in the midst of every $2^{nd}$ clearance period.

Figure 1:
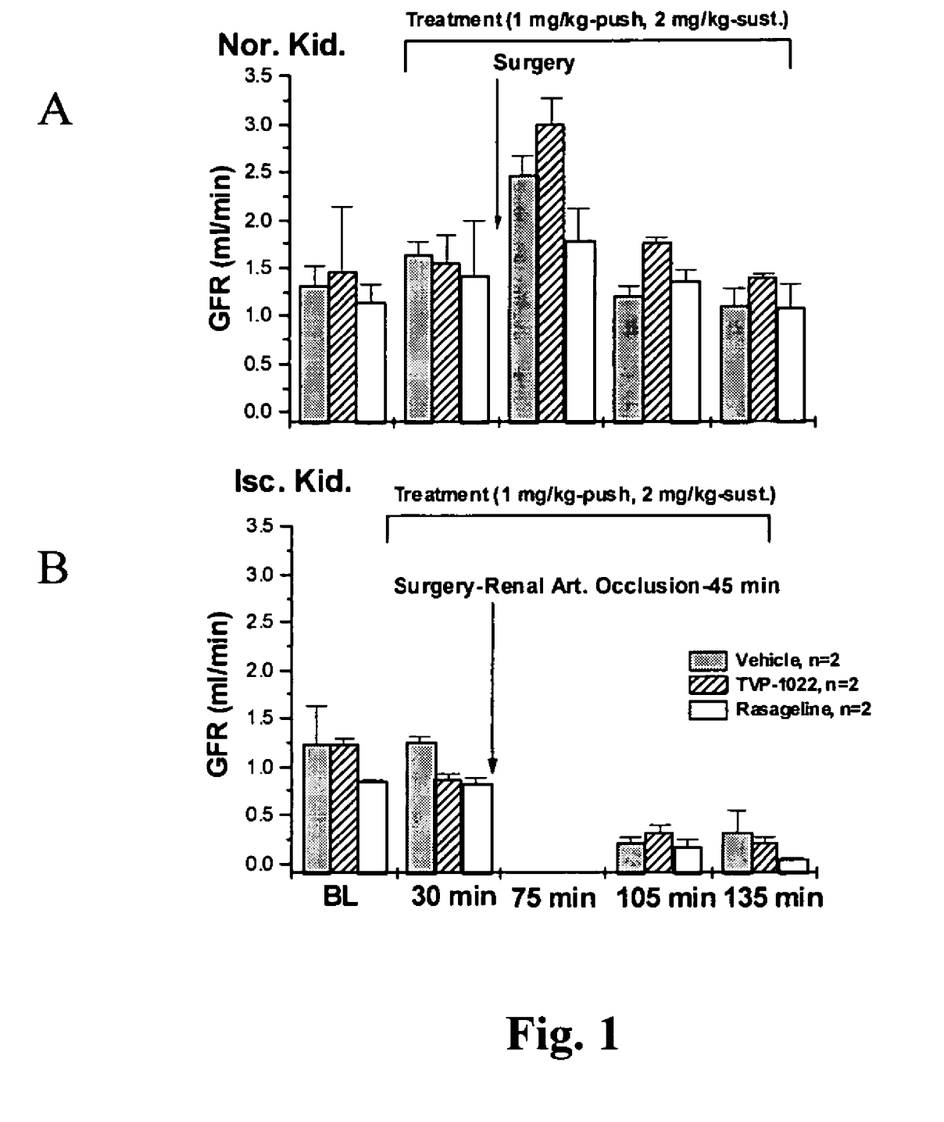
FIGS. 1A-1B show the effects of pretreatment with rasagiline or S-(−)-N-propargyl-1-aminoindan (TVP-1022) (1 mg/kg), 30 minutes prior to the induction of renal ischemia in rats, on the glomerular filtration rate (GFR) of the normal (1A) and ischemic (1B) kidney.
Figure 2:
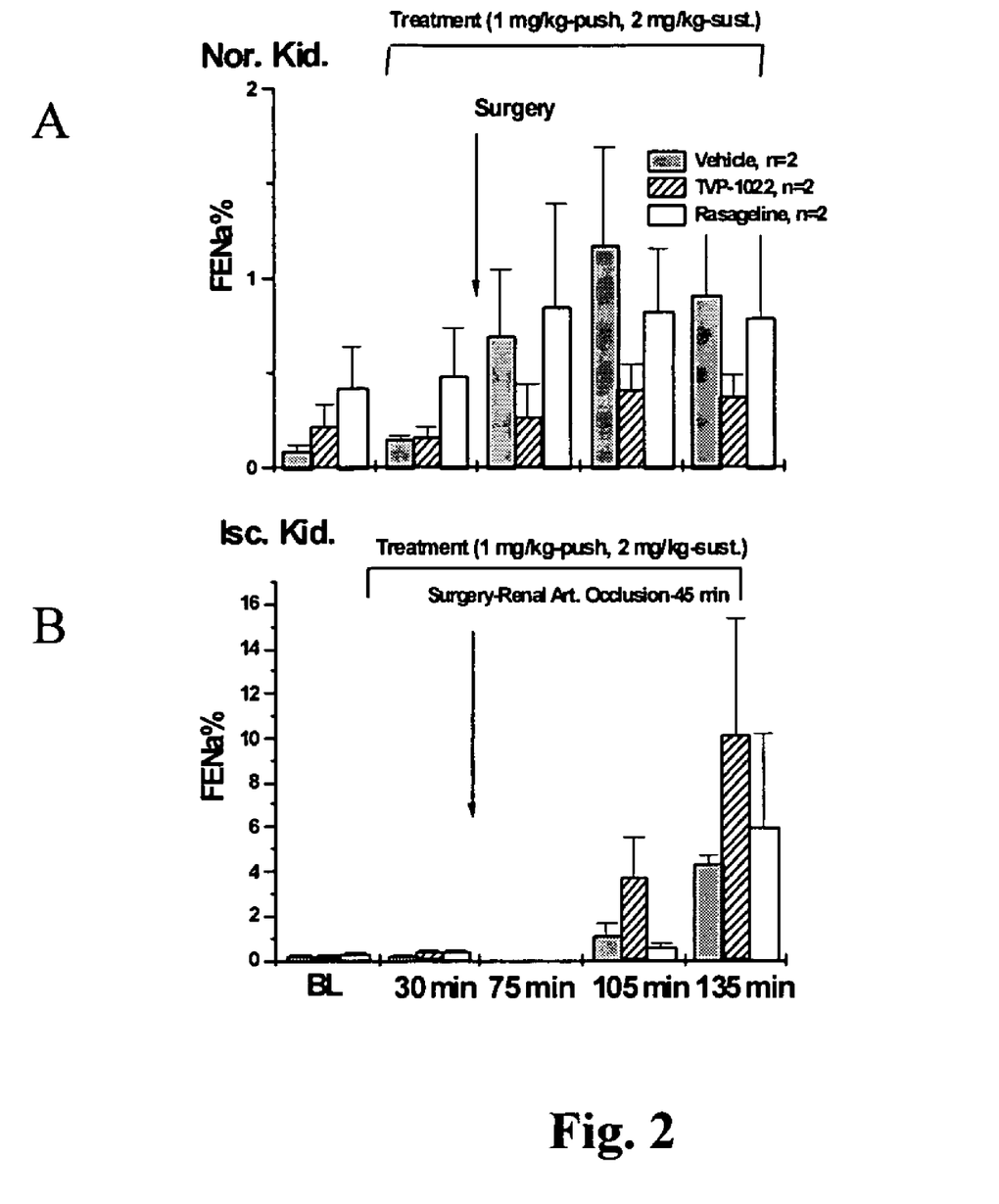
FIGS. 2A-2B show the effects of pretreatment with rasagiline or S-(−)-N-propargyl-1-aminoindan (1 mg/kg), 30 minutes prior to the induction of renal ischemia in rats, on the fractional excretion of sodium (FENa) of the normal (2A) and ischemic (2B) kidney.

As shown in FIGS. 1A-1B, it seems that S-(−)-N-propargyl-1-aminoindan, and to a lesser extent rasagiline, improved the function of the ischemic kidney as well as the function of the control normal kidney. FIG. 2A shows that S-(−)-N-propargyl-1-aminoindan, and to a greater extent rasagiline, increased the fractional excretion of $Na^+$ (FENa) by normal kidney. In contrast, S-(−)-N-propargyl-1-aminoindan enhanced FENa by ischemic kidney more than rasagiline (FIG. 2B).

Example 2

Chronic Studies—Effects of Chronic Administration of Rasagiline or S-(−)-N-propargyl-1-aminoindan on Sodium Excretion in Rats with Heart Failure This protocol was designed to evaluate the effects of long-term administration (14 days) of rasagiline or S-(−)-N-propargyl-1-aminoindan on renal clearance and excretory parameters in rats with experimental congestive heart failure induced by the placement of an arterio-venous fistula between the abdominal aorta and the inferior vena-cava as described previously (Abassi et al., 1990).

In short, the abdominal aorta and inferior vena-cava were exposed through a mid-abdominal incision under pentobarbital anesthesia (60 mg/kg, I.P.), and an arterio-venous shunt was surgically created in the common wall of the two vessels (side to side, 1.2 mm O.D.). Following surgery, the rats were allowed to recover and housed in individual metabolic cages for measurements of daily urine volume and urinary sodium/potassium excretion.

Rasagiline or S-(−)-N-propargyl-1-aminoindan were dissolved in drinking water and given orally at a dose of 1 or 7.5 mg/kg/day for 5 days to normal rats. Following this period, the animals were subjected either to sham operation (n=6) or to creation of aortocaval fistula (ACF) (n=6) as described above. These experimental groups were treated daily by gavage with 1 or 7.5 mg/kg of rasagiline or S-(−)-N-propargyl-1-aminoindan for additional 14 days, and their daily urine volume, sodium and potassium excretion were measured. Rats treated with vehicle (water) served as controls. After completion of the treatment period, animals from the different experimental groups were killed by decapitation and their blood was collected in pre-cooled tubes. Rats with sham operation or animals with arterio-venous fistula treated with vehicle served as controls.

Figure 3:
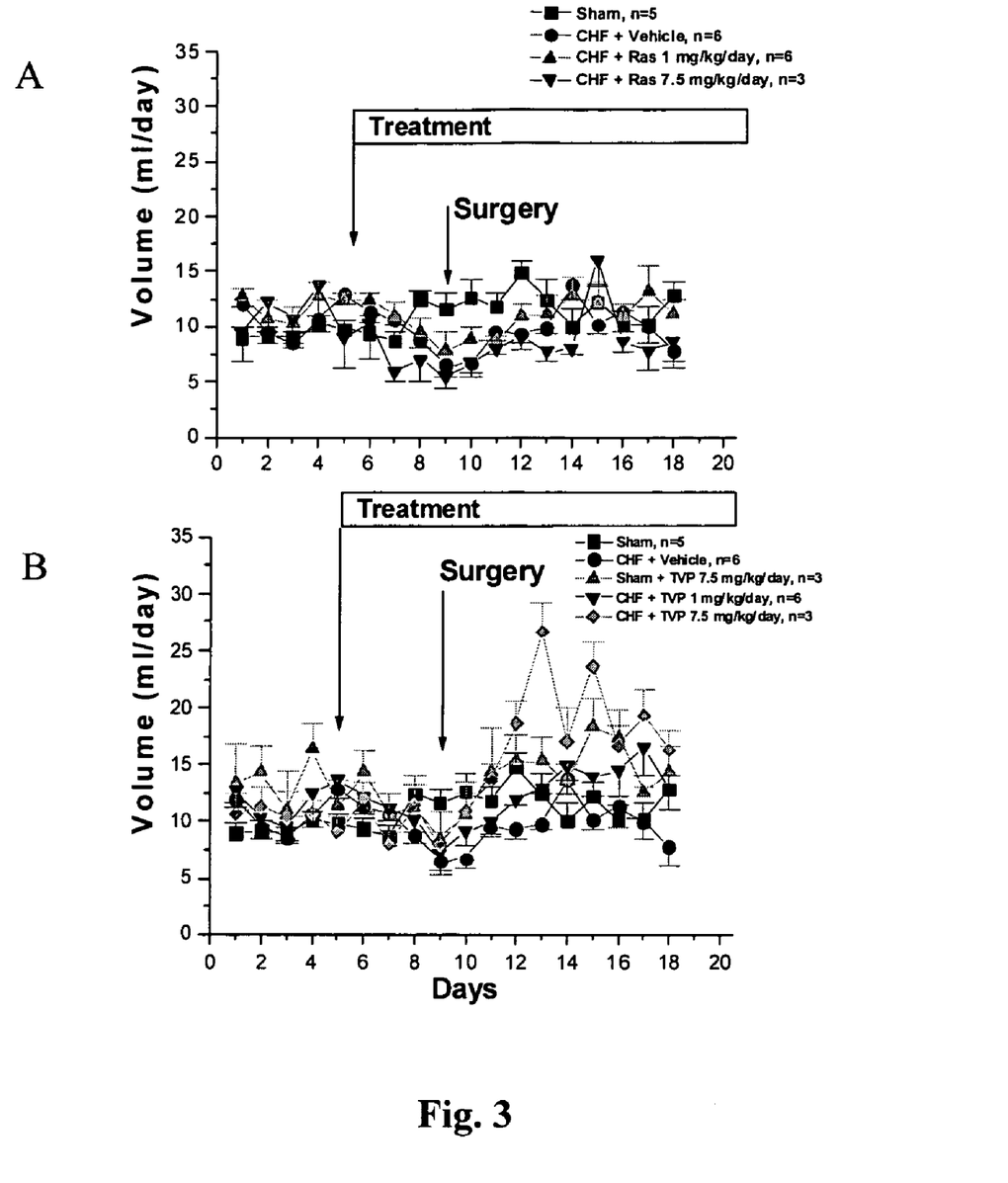
FIGS. 3A-3B show the effect of chronic treatment with rasagiline (3A) or S-(−)-N-propargyl-1-aminoindan (3B) on daily urine volume in rats with CHF and in sham operated animals.
Figure 4:
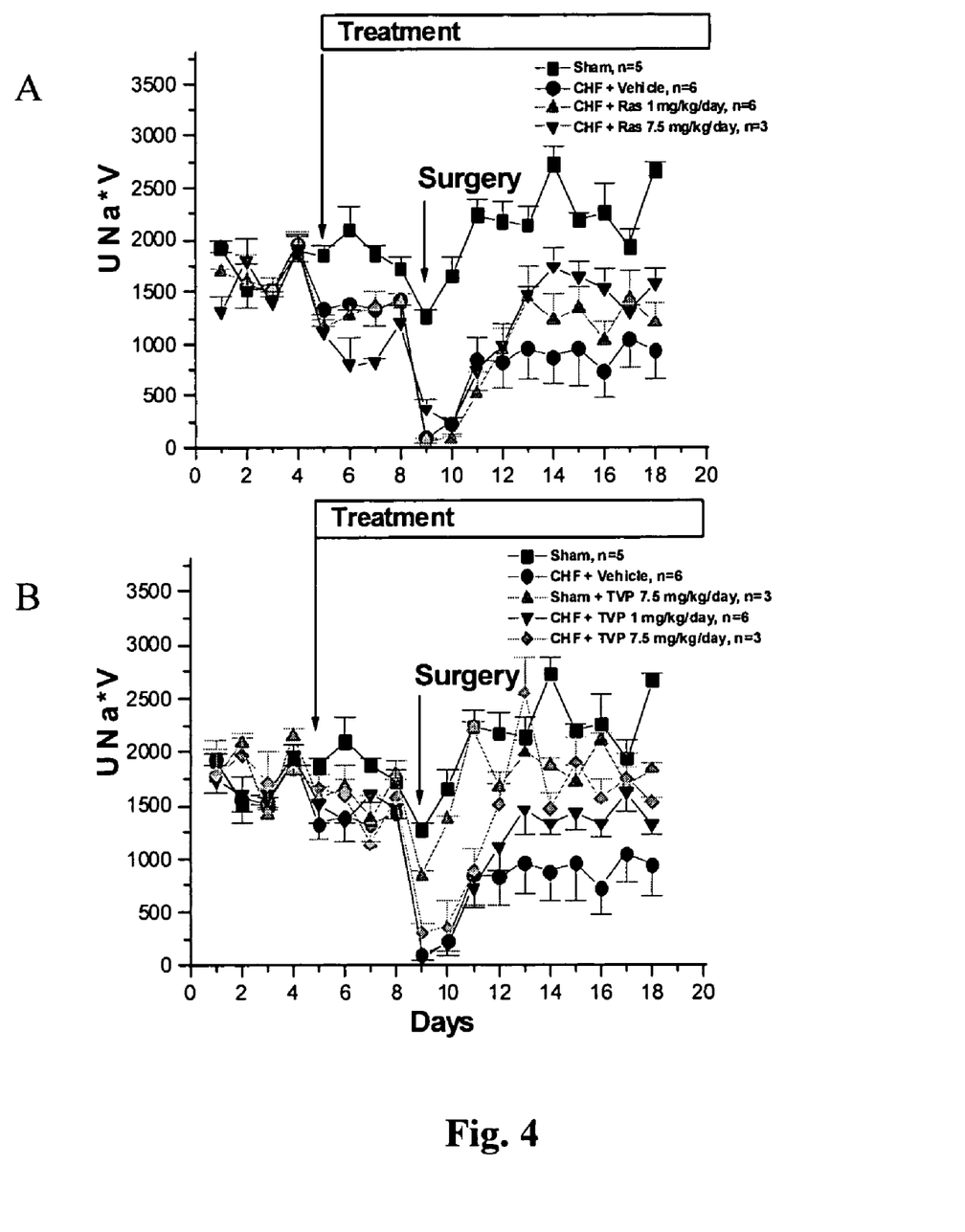
FIGS. 4A-4B show the effects of chronic treatment with rasagiline (4A) or S-(−)-N-propargyl-1-aminoindan (4B) at doses of 1 or 7.5 mg/kg/day on the daily sodium excretion in rats with CHF and in sham operated animals.
Figure 5:
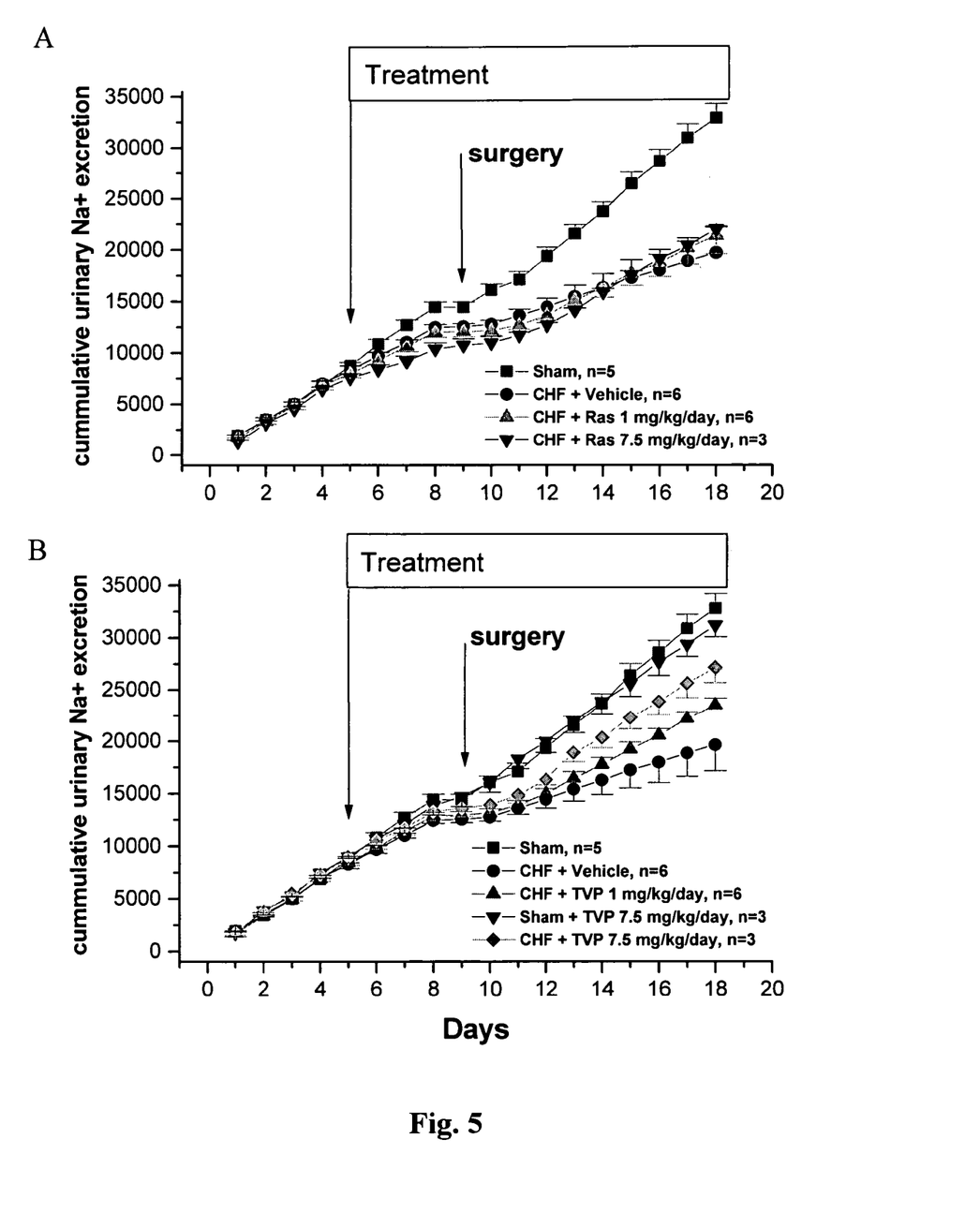
FIGS. 5A-5B show the effects of chronic treatment with rasagiline (5A) or S-(−)-N-propargyl-1-aminoindan (5B) at doses of 1 or 7.5 mg/kg/day on the cumulative sodium excretion in rats with CHF and in sham operated animals.
Figure 6:
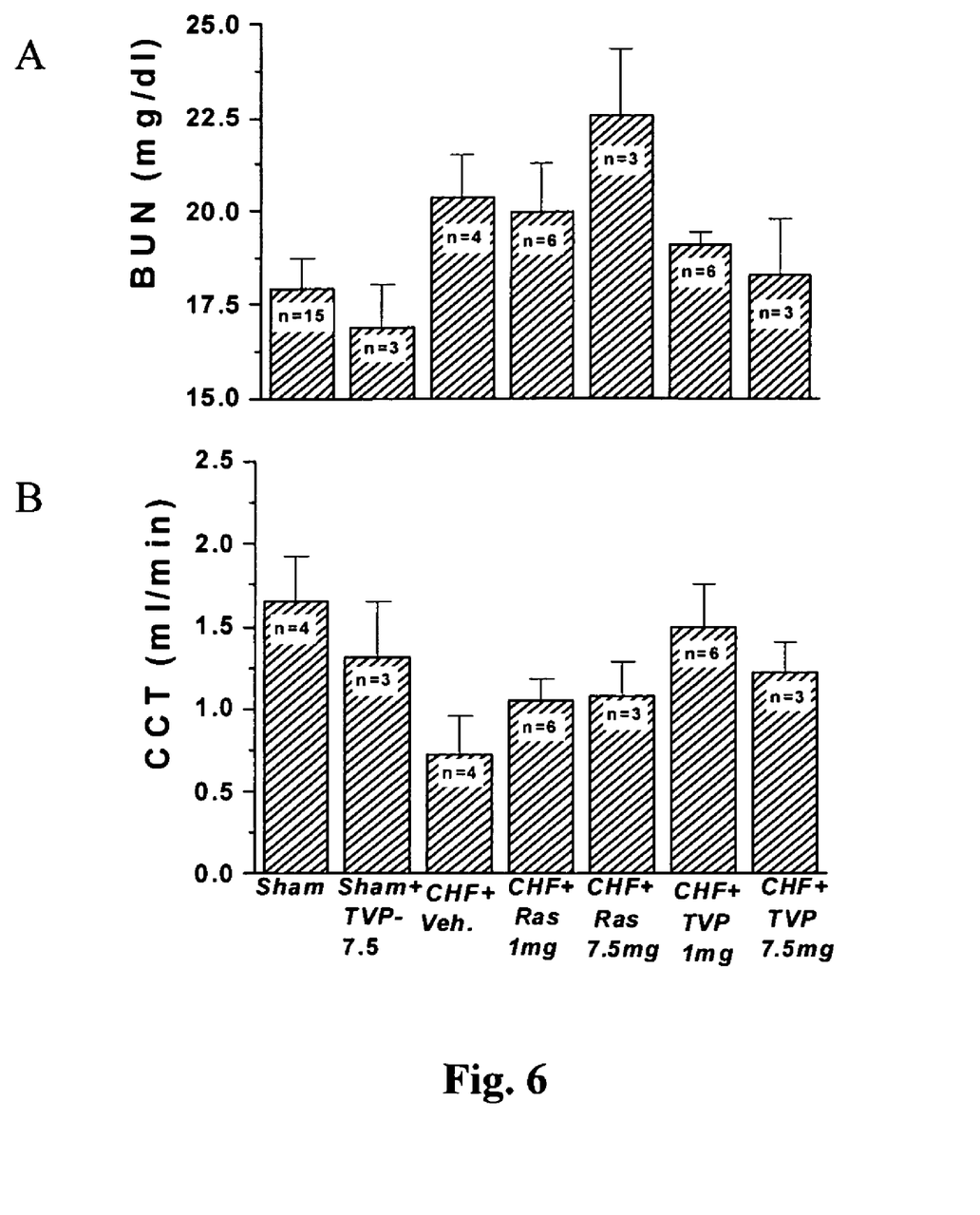
FIGS. 6A-6B show the effects of chronic treatment with rasagiline or S-(−)-N-propargyl-1-aminoindan on blood urea nitrogen (BUN) (6A) and on creatinine clearance test (CCT=GFR) (6B) in rats with CHF. These drugs were given chronically to rats with A-V fistula via gavage, at doses of 1 or 7.5 mg/kg/day for 2 weeks.

As shown in FIGS. 3A-3B, chronic administration of S-(−)-N-propargyl-1-aminoindan, but not of rasagiline, to rats with CHF increased the urinary flow rate. Similarly, the absolute and cumulative urinary sodium excretions (FIGS. 4 and 5, respectively) were markedly enhanced by S-(−)-N-propargyl-1-aminoindan and, to a lesser extent, by rasagiline. As shown in FIG. 6, these effects were associated with enhanced GFR, suggesting that S-(−)-N-propargyl-1-aminoindan can improve kidney function in heart failure disease state.

References

Abassi, Z., Haramati, A., Hoffman, A., Burnett Jr, J. C., Winaver, J., Effect of converting-enzyme inhibition on renal response to ANF in rats with experimental heart failure, *Am J Physiol.*, 1990, 259, R84-R89

Abu-Raya, S., Tabakman, R., Blaugrund, E., Trembovler, V., Lazarovici, P., Neuroprotective and neurotoxic effects of monoamine oxidase-B inhibitors and derived metabolites under ischemia in PC12 cells, *Eur. J. Pharmacol.*, 2002, 434, 109-116

Am, O. B., Amit, T., Youdim, M. B. H., Contrasting neuroprotective and neurotoxic actions of respective metabolites of anti-Parkinson drugs rasagiline and selegiline, *Neurosci. Lett.*, 2004, 355, 169-172

Arendshorst, W. J., Finn, W. F., Gottschalk, C. W., Pathogenesis of acute renal failure following temporary renal ischemia in the rat, *Circ Res*, 1975, 37, 558-568

Birkmayer, W., Riederer, P., Youdim, M. B. H., Linauer, W., The potentiation of anti-akinetic effect after L-dopa treatment by an inhibitor of MAO-B deprenyl, *J. Neural. Transm.*, 1975, 36, 303-326

Birkmayer, W., Riederer, P., Ambrozi, L., Youdim, M. B. H., Implications of combined treatment with madopar and 1-deprenyl in Parkinson's disease, *Lancet.*, 1977, 2, 439-443

Brodsky, S., Gurbanov, K., Abassi, Z., Hoffman, A., Ruffolo Jr, R. R., Feuerstein, G. Z., Winaver, J. Effects of eprosartan on renal function and cardiac hypertrophy in rats with experimental heart failure, *Hypertension*, 1998, 32, 746-752

Brooks, D. J., Sagar, H., UK-Irish Entacapone Study Group. Entacapone is beneficial in both fluctuating and non-fluctuating patients with Parkinson's disease: a randomized, placebo controlled, double blind, six month study, *J. Neurol. Neurosurg. Psychiatry*, 2003, 74, 1071-1079

Canavese, C., Strattaand, P., Vercellone, A., The case for oxygen free radicals in the pathogenesis of ischemic acute renal failure, *Nephron*, 1988, 49, 9-15

Chien, K. R., Stress pathways and heart failure, *Cell*, 1999, 98, 555-558

Cristol, J. P., Thiemermann, C., Mitchell, A., Walder, C., Vane, J. R., Support of renal blood flow after ischemic-reperfusion injury by endogenous formation of nitric oxide and of cyclo-oxygenase vasodilator metabolites, *Br J Pharmacol*, 1993, 109, 188-194 de Simone, G., McClelland, R., Gottdiener, J. S., Celentano, A., Kronmal, R. A., Gardin, J. M., Relation of hemodynamics and risk factors to ventricular-vascular interactions in the elderly: the Cardiovascular Health Study, *J Hypertens.*, 2003, 19, 1893-1903

Dzau, V. J., Renal and circulatory mechanisms in congestive heart failure, *Kidney Int.*, 1987, 31, 1402-1415

Finberg, J. P., Ari, G., Lavian, G., Hovevey-Sion, D., Modification of alpha-2 presynaptic receptor activity and catecholamine release following chronic MAO inhibition, *J Neural Transm Suppl.*, 1990, 32, 405-412

Finberg, J. P. M., Lamensdorf, I., Weinstock, M., Schwartz, M., Youdim, M. B. H., Pharmacology of rasagiline (N-propargyl-IR-aminoindan), *Adv. Neurol.*, 1999, 80, 495-501

Finberg, J. P., Youdim, M. B. H., Pharmacological properties of the anti-Parkinson drug rasagiline; modification of endogenous brain amines, reserpine reversal, serotonergic and dopaminergic behaviors, *Neuropharmacology*, 2002, 43, 1110-1118

Gassen, M., Lamensdorf, I., Armony, T., Finberg, J. P., Youdim, M. B. H., Attenuation of methamphetamine induced dopaminergic neurotoxicity by flupirtine: microdialysis study on dopamine release and free radical generation. *J. Neural. Transm.*, 2003, 110, 171-182

Glezer, S., Finberg, J. P., Pharmacological comparison between the actions of methamphetamine and 1-aminoindan stereoisomers on sympathetic nervous function in rat vas deferens, *Eur. J. Pharmacol.*, 2003, 472, 173-177

Green, J., Abassi, Z., Winaver, J., Skorecki, K., Acute renal failure: clinical and pathophysiological aspects. In *The Kidney: Physiology and Pathophysiology*, 3rd edition, 2000, edited by D. W. Seldin and G. Giebisch. Philadelphia: Lippincott-Raven Greene, E. L., Paller, M. S., Oxygen free radicals in acute renal failure. *Miner Electrolyte Metab.*, 1991, 17, 124-132

Hostetter, T. H., Pfeffer, J. M., Pfeffer, M. A., Dworkin, L. D., Braunwald, E., Brenner, B. M., Cardiorenal hemodynamics and sodium excretion in rats with myocardial infarction. *Am J Physiol.*, 1983, 245, H98-H103

Kraemer, T., Maurer, H. H., Toxicokinetics of amphetamines: metabolism and toxicokinetic data of designer drugs, amphetamine, methamphetamine, and their N-alkyl derivatives. *Ther. Drug. Monit.*, 2002, 24, 277-289

Kribben, A., Edelstein, C. L., Schrier, R. W., Pathophysiology of acute renal failure. *J. Nephrol.*, 1999, 12 (Suppl. 2), S142-S151

Lavian, G., Finberg, J. P., Youdim, M. B. H., The advent of a new generation of monoamine oxidase inhibitor antidepressants: pharmacologic studies with moclobemide and brofaromine, *Clin. Neuropharmacol.*, 1993, 16 (Suppl. 2), S1-7

Lees, A., Show, K. M., Kahout, L. J., Stern, G., Elsworth, J. D., Sandler, M., Youdim, M. B. H., Deprenyl in Parkinson's Disease, *Lancet*, 1977, 2, 791-795

Lees, A. J., Comparison of therapeutic effects and mortality data of levodopa and levodopa combined with selegiline in patients with early, mild Parkinson's disease. Parkinson Disease Research Group of the United Kingdom, *Br. Med. J.*, 1995, 311, 1601-1607

Mandel, S., Grunblatt, E., Riederer, P., Gerlach, M., Levites, Y., Youdim, M. B. H., Neuroprotective strategies in Parkinson's disease: an update on progress, *CNS. Drugs.*, 2003, 17, 729-762

Meerson, F. Z., Pshennikova, M. G., Malyshev, I. Y., Adaptive defense of the organism. Architecture of the structural trace and cross protective effects of adaptation, Ann NY Acad Sci., 1996, 793, 371-385

Parkinson Study Group (Datatop), Selegiline and Parkinson's disease. *N. Engl. J. Med.*, 1989, 321, 1364-1371

Parkinson Study Group, A controlled trial of rasagiline in early Parkinson disease: the TEMPO Study. *Arch. Neurol.*, 2002, 59, 1937-1943

Reynolds, G. P., Riederer, P., Sandler, N. R., Jellinger, K. Seemali, D., Amphetamine and 2-phenylethylamine in post mortem Parkinson brains after 1-deprenyl administration, *J. Neural. Transm.*, 1978, 43, 271-278

Riederer, P. Rinne, U. K., Selegiline in Parkinson's disease: An update, *Mov. Disords.*, 1992, 8 (Suppl. 1), 51-54

Schrier, R. W., Wang, W., Poole, B., Mitra, A., Acute renal failure: definitions, diagnosis, pathogenesis and therapy, *J. Clin. Invest.*, 2004, 114, 5-14

Shin, H. S., Metabolism of selegiline in humans: Identification, excretion and stereochemistry of urine metabolites, *Drug. Metab. Dispos.*, 1997, 25, 657-662

Simpson, L. L., Evidence that deprenyl, a type B monoamine oxidase inhibitor is an indirectly acting sympathomimetic amine, *Biochem. Pharmacol.*, 1978, 27, 1591-1595

Stumpe, K. O., Solle, H., Klein, H., Kruck, F., Mechanism of sodium and water retention in rats with experimental heart failure, *Kidney Int*, 1973, 4, 309-317

Swynghedauw, B., Baillard, C., Biology of hypertensive cardiopathy, *Curr Opin Cardiol.*, 2000, 15, 247-253

Szoko, E., Kalasz, H., Magyat, K., Biotransformation of deprenyl enantiomers, *Eur. J. Drug. Metab. Pharmacokinet.*, 1999, 24, 315-319

Youdim, M. B. H., Gross, A., Finberg, J. P., Rasagiline [N-propargyl-1R(+)-aminoindan], a selective and potent inhibitor of mitochondrial monoamine oxidase B, *Br. J. Pharmacol.*, 2001, 132, 500-506

Youdim, M. B. H., Rasagiline: an antiparkinson drug with neutroprotective activity, *Expert. Rev., Neurotherapeutics*, 2003, 3, 737-749

Watkins, L., Burton, J. A., Haber, E., Cant, J. R., Smith, F. W., Barger, A. C., The renin-angiotensin-aldosterone system in congestive heart failure in conscious dogs, *J Clin Invest*, 1976, 57, 1606-1617

The invention claimed is:

1. A method for treatment of a person diagnosed as suffering from acute renal failure, which comprises
administering to the person an effective amount therefor of S-(−)-N-propargyl-1-aminoindan or a pharmaceutically acceptable salt thereof.

2. The method of claim 1, wherein S-(−)-N-propargyl-1-aminoindan is administered.

3. The method of claim 1, wherein said pharmaceutically acceptable salt of S-(−)-N-propargyl-1-aminoindan is administered.

4. The method of claim 3, wherein said pharmaceutically acceptable salt is selected from the group consisting of the mesylate salt; the esylate salt; the sulfate salt; and the hydrochloride salt of S-(−)-N-propargyl-1-aminoindan.

5. A method for treatment of a subject diagnosed as being susceptible to acute renal failure which comprises administering to the subject an effective amount therefor of S-(−)-N-propargyl-1-aminoindan or a pharmaceutically acceptable salt thereof,
wherein said subject susceptible to acute renal failure is a subject exposed to (i) a therapeutic agent selected from the group consisting of cyclosporines, aminoglycosides, nonsteroidal antiinflammatory drugs, cisplatin and amphotericin B; (ii) contrast agents; or (iii) heavy metals or organic solvents.

6. The method of claim 5, wherein S-(−)-N-propargyl-1-aminoindan is administered.

7. The method of claim 5, wherein said pharmaceutically acceptable salt of S-(−)-N-propargyl-1-aminoindan is administered.

8. The method of claim 7, wherein said pharmaceutically acceptable salt is selected from the group consisting of the mesylate salt; the esylate salt; the sulfate salt; and the hydrochloride salt of S-(−)-N-propargyl-1-aminoindan.

9. The method of claim 5, wherein said subject susceptible to acute renal failure is a diabetic patient or a subject suffering from congestive heart failure.

10. A method for improving the function of an ischemic kidney in a subject suffering from acute renal failure, which comprises administering to the subject an effective amount therefor of S-(−)-N-propargyl-1-aminoindan or a pharmaceutically acceptable salt thereof.

11. A method for improving the function of a kidney in a subject diagnosed as being susceptible to acute renal failure, which comprises administering to the subject an effective amount therefor of S-(−)-N-propargyl-1-aminoindan or a pharmaceutically acceptable salt thereof,
wherein said subject susceptible to acute renal failure is a subject exposed to (i) a therapeutic agent selected from the group consisting of cyclosporines, aminoglycosides, nonsteroidal antiinflammatory drugs, cisplatin and amphotericin B; (ii) contrast agents; or (iii) heavy metals or organic solvents.

12. A method for attenuating deterioration of kidney function in a subject diagnosed as being susceptible to acute renal failure, which comprises administering to the subject an effective amount therefor of S-(−)-N-propargyl-1-aminoindan or a pharmaceutically acceptable salt thereof,
wherein said subject susceptible to acute renal failure is a subject exposed to (i) a therapeutic agent selected from the group consisting of cyclosporines, aminoglycosides, nonsteroidal antiinflammatory drugs, cisplatin and amphotericin B; (ii) contrast agents; or (iii) heavy metals or organic solvents.

\* \* \* \* \*

UNITED STATES PATENT AND TRADEMARK OFFICE
CERTIFICATE OF CORRECTION

PATENT NO. : 8,263,655 B2  Page 1 of 1
APPLICATION NO. : 11/244150
DATED : September 11, 2012
INVENTOR(S) : Binah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 635 days.

Signed and Sealed this
Twenty-ninth Day of December, 2015

Michelle K. Lee
*Director of the United States Patent and Trademark Office*